(12) United States Patent
Shuros et al.

(10) Patent No.: US 8,105,261 B2
(45) Date of Patent: Jan. 31, 2012

(54) OSMOTIC DEVICES AND METHODS FOR DIURETIC THERAPY

(75) Inventors: Allan Charles Shuros, St. Paul, MN (US); Eric A. Mokelke, White Bear Lake, MN (US); Michael John Kane, Lake Elmo, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 984 days.

(21) Appl. No.: 11/772,397

(22) Filed: Jul. 2, 2007

(65) Prior Publication Data

US 2009/0012444 A1    Jan. 8, 2009

(51) Int. Cl.
A61M 37/00 (2006.01)
A61M 31/00 (2006.01)

(52) U.S. Cl. .................. 604/6.09; 604/103.01

(58) Field of Classification Search ........ 604/4.01–6.16, 604/31, 82, 96.01, 97.01, 98.01, 99.01, 99.02, 604/99.04, 192, 523, 915, 920, 103.01; 600/585
See application file for complete search history.

(56) References Cited

U.S. PATENT DOCUMENTS

| | | | |
|---|---|---|---|
| 5,388,449 A | 2/1995 | LeVeen et al. | |
| 5,492,532 A * | 2/1996 | Ryan et al. | 604/103.09 |
| 6,237,398 B1 | 5/2001 | Porat et al. | |
| 6,656,151 B1 * | 12/2003 | Blatter | 604/96.01 |
| 6,692,528 B2 | 2/2004 | Ward et al. | |

(Continued)

FOREIGN PATENT DOCUMENTS

DE 10302241 8/2004

(Continued)

OTHER PUBLICATIONS

International Search Report from International application No. PCT/US2007/074502.

(Continued)

*Primary Examiner* — Leslie Deak
*Assistant Examiner* — Philip R West
(74) *Attorney, Agent, or Firm* — Pauly, DeVries, Smith & Deffner, L.L.C.

(57) ABSTRACT

Embodiments of the invention are related to devices and methods for modulating renal function, amongst other things. In an embodiment, the invention includes an implantable occlusive device including a wall member defining an enclosed volume, the wall member can include a semi-permeable membrane. The device can also include a solution comprising a solvent and a solute disposed within the enclosed volume of the wall member. The semi-permeable membrane can be permeable to the solvent and impermeable to the solute. The enclosed volume can be configured to expand and contract in response to changes in the osmolality of a bodily fluid. The device can include a positioning member configured to maintain the position of the implantable occlusive device relative to a lengthwise axis of a lymphatic vessel. In an embodiment, the invention includes a method of modulating renal function in a patient including implanting an occlusive device in the patient, the occlusive device comprising a semi-permeable membrane and configured to expand or contract based on the passage of a fluid across the semi-permeable membrane. Other aspects and embodiments are provided herein.

16 Claims, 11 Drawing Sheets

U.S. PATENT DOCUMENTS

| | | |
|---|---|---|
| 6,978,182 B2 | 12/2005 | Mazar et al. |
| 7,526,337 B2 | 4/2009 | Shuros et al. |
| 7,664,548 B2 | 2/2010 | Amurthur et al. |
| 7,734,341 B2 | 6/2010 | Shuros |
| 7,824,369 B2 * | 11/2010 | Cangialosi ................. 604/96.01 |
| 7,894,906 B2 | 2/2011 | Shuros |
| 7,940,293 B2 | 5/2011 | Gorzynski |
| 2006/0058833 A1 | 3/2006 | VanCamp et al. |
| 2006/0173252 A1 | 8/2006 | Ellingsen et al. |
| 2008/0114408 A1 | 5/2008 | Shuros et al. |

FOREIGN PATENT DOCUMENTS

| | | |
|---|---|---|
| EP | 1707233 | 10/2006 |
| WO | WO-2009005529 | 1/2009 |

OTHER PUBLICATIONS

Ishikawa, et al., "The Human Renal Lymphatics Under Normal and Pathological Conditions", Histopathology 2006, 49:265-273.

Shotan, et al., "Fluid Overload Contributing to Heart Failure", Nephrol Dial Transplant 2005, Suppl. 7:vii24-vii27.

Han, et al., "Constant-Volume Hydrogel Osmometer: A New Device Concept for Miniature Biosensors", Biomacromolecules 2002, 3:1271-1275.

Wilcox, et al., "Renal Interstitial Pressure and Sodium Excretion During Hilar Lymphatic Ligation", Am. J. Physiol. Renal Physiol. 1984, 247:F344.

Stolarczyk, J et al., "Effects of Renal Lymphatic Occlusion and Venus Constriction on Renal Function", Am. J. Path. 1975, 78:285-295.

O'Morchoe, C et al., "Renal Contribution to Thoracic Duct Lymph in Dogs", J. Physiol. 1968, 194:305-315.

"Office Action Received", from JP Application No. 2010-514743, corresponding to U.S. Appl. No. 11/772,397, mailed Mar. 28, 2011, (pp. 1-2).

"PCT Notification Concerning Transmittal of International Preliminary Report on Patentability", from International Application No. PCT/US2007/074502, corresponding to U.S. Appl. No. 11/772,397, mailed Jan. 14, 2010, pp. 1-5.

"Response to Japanese Office Action", Response to Japanese Office Action dated Mar. 28, 2011, Filed in the Japanese Patent Office on Jun. 17, 2011 for Japanese Patent Application No. 200480020047.9, corresponding to U.S. Appl. No. 11/772,397, (pp. 9).

* cited by examiner

OSMOTIC DEVICES AND METHODS FOR DIURETIC THERAPY

TECHNICAL FIELD

This disclosure relates generally to devices and methods for modulating renal function and, more particularly, to occlusive devices and methods for modulating renal function, amongst other things.

BACKGROUND OF THE INVENTION

The kidneys function to rid the body of metabolic and ingested waste products and to maintain the volume and composition of bodily fluids. The maintenance of a constant extracellular fluid (ECF) composition by the kidneys is accomplished by various neural, hormonal, and intrinsic homeostatic mechanisms that control the rate at which blood is filtered by the glomerulis, referred to as the glomerular filtration rate (GFR), and the extent to which sodium and water are reabsorbed from the filtrate into the peritubular capillary blood.

The kidneys normally act to maintain both arterial blood pressure and ECF volume within desired normal ranges. However, in certain pathological situations, homeostatic mechanisms do not respond in an appropriate manner. One situation in which the homeostatic mechanisms of the kidneys may not respond in an optimal manner is during heart failure. Heart failure refers to a clinical syndrome in which an abnormality of cardiac function causes a below normal or normal ejection fraction and pathophysiological ventricular hypertrophy which often results in reduction in cardiac output. Such a reduction in cardiac output can fall below a level adequate to meet the metabolic demand of peripheral tissues. Reduced cardiac output has a depressing effect on renal function due to decreased renal perfusion, which causes a reduction in salt and water excretion by the pressure natriuresis mechanism. The renin-angiotensin-aldosterone system also promotes water and plasma volume retention to compensate for the reduced cardiac output. The increased sympathetic activity in response to low blood pressure and/or cardiac output may also depress renal function still further.

The increased fluid retention by the kidneys results in an increased blood volume and further increased venous return to the heart, thus increasing the heart's preload. This process is acutely beneficial in supplementing and maintaining adequate cardiac output, however this process can result in deleterious changes long-term. Increased fluid retention causes the progressive peripheral and pulmonary edema that characterizes overt congestive heart failure. As part of downward spiral, diastolic filling pressure becomes further elevated which causes the heart to become so dilated and edematous that its pumping function deteriorates even more.

One approach to treating heart failure is to modulate renal function through pharmacological means. For example, diuretic drugs can be used to decrease the tubular reabsorption of salt and water, leading to reduced fluid retention (increased fluid excretion). However, such pharmacological agents are not always effective and they may cause significant side effects. In addition, patient compliance with pharmacological regimens is a serious problem.

For at least these reasons, a need exists for devices and methods for modulating renal function.

SUMMARY OF THE INVENTION

Embodiments of the invention are related to modulating renal function, amongst other things. In an embodiment, the invention includes an implantable occlusive device including a wall member defining an enclosed volume, the wall member comprising a semi-permeable membrane. The device can also include a solution comprising a solvent and a solute disposed within the enclosed volume of the wall member. The semi-permeable membrane can be permeable to the solvent and impermeable to the solute. The enclosed volume can be configured to expand in response to decreases in osmolality of a bodily fluid and contract in response to increases in osmolality of a bodily fluid. The device can include a positioning member configured to maintain the position of the implantable occlusive device relative to a lengthwise axis of a lymphatic vessel.

In an embodiment, the invention includes a method of modulating renal function in a patient including implanting an occlusive device in the patient, the occlusive device comprising a semi-permeable membrane and configured to expand or contract based on the passage of a fluid across the semi-permeable membrane. The method can further include occluding a renal lymphatic vessel with the occlusive device.

In an embodiment, the invention includes a method of treating heart failure decompensation including implanting an occlusive device in the patient, the occlusive device comprising a semi-permeable membrane and configured to expand or contract or change its shape based on the passage of a fluid across the semi-permeable membrane. The method can further include occluding a renal lymphatic vessel with the occlusive device.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

Blocking renal lymphatic flow can modulate renal function. Specifically, blocking renal lymphatic flow can decrease fluid retention by the kidneys, or stated differently, increase the amount of fluid excreted from the body as urine. This diuresis is typically the goal of diuretic pharmacological therapy. Embodiments of the invention can include devices that occlude the renal lymphatic vessels, thereby blocking or reducing renal lymphatic flow. As such, embodiments of the invention can be used to stimulate urine production and excretion by the kidneys (decrease fluid retention by the kidneys). Some embodiments can include treating disease states, such as heart failure and/or hypertension.

Embodiments of devices included herein can include those with an element that changes in physical dimensions through the process of osmosis. Osmosis is a physical process in which a solvent moves, without input of energy, across a semi-permeable membrane (permeable to the solvent, but not a solute) separating two solutions having different solute concentrations. Net movement of solvent is from the less-concentrated (hypotonic) solution, to the more-concentrated (hypertonic) solution.

Figure 1:
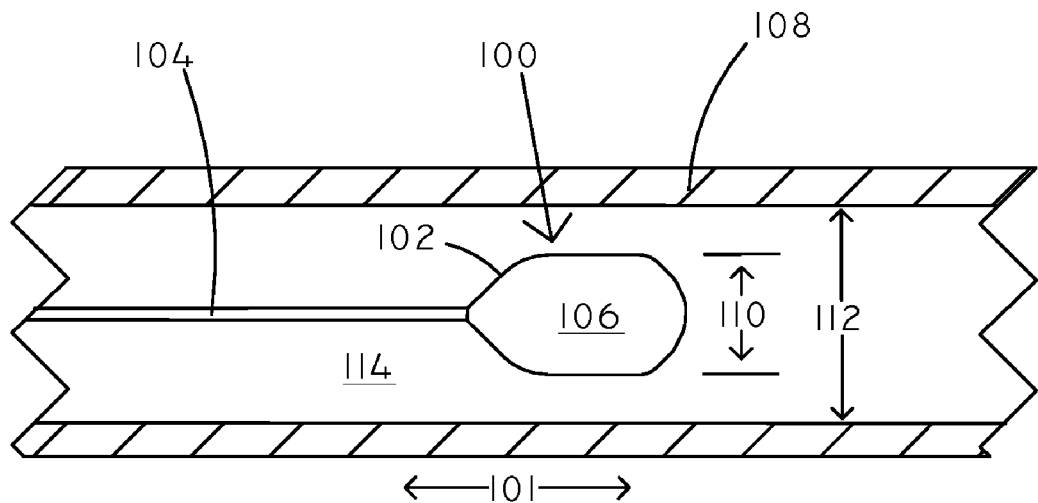
FIG. 1 is a schematic view of an occlusive device disposed within the lumen of a lymphatic vessel in accordance with an embodiment of the invention.

Referring now to FIG. 1, a schematic view is shown of an occlusive device 100 disposed within the lumen 114 of a renal lymphatic vessel 108 in accordance with an embodiment of the invention. A wall member 102 including a semi-permeable membrane encloses an enclosed volume 106. The wall member 102 is attached to a lead member 104 or tether. The lead member 104 can serve to maintain the position of the occlusive device 100 within the lymphatic vessel 108. The lead member 104 can serve as one example of a positioning member since it can serve to maintain the position of the occlusive device relative to the lengthwise axis of the lymphatic vessel (axis of fluid flow) in which it can occlude fluid flow. The lengthwise axis of the renal lymphatic vessel 108 is indicated by arrowed line 101.

A solution including a solvent and a solute is disposed within the enclosed volume 106. In some embodiments, the solvent is water. The solute can include many different types of chemical compounds. In an embodiment, the solute is a biocompatible chemical compound. In an embodiment, the solute is a chemical compound naturally occurring within the body. In an embodiment, the solute is sodium chloride. In an embodiment, the solute is glucose. Further examples of solutes are described below.

The enclosed volume 106 can change in size as a result of osmosis. Specifically, where the solution within the enclosed volume 106 has a higher osmolality than the bodily fluid within the lumen 114 of the lymphatic vessel 108, fluid can diffuse across the semi-permeable membrane and into the enclosed volume 106, causing the same to enlarge. Conversely, where the solution within the enclosed volume 106 has a lower osmolality than the bodily fluid within the lumen 114 of the lymphatic vessel 108, fluid can diffuse across the semi-permeable membrane and out of the enclosed volume 106, causing the same to become smaller. Between about 280 and 303 mOsm/kg is a normal value of osmolality in fluids of the body. As such, in some embodiments, the solution within the enclosed volume has a starting osmolality of between about 280 and 303 mOsm/kg when the device is implanted within a patient. In other embodiments, the solution within the enclosed volume can have a starting osmolality outside of that range.

Though units of osmolality are used herein to describe concentrations of solutions, it will be appreciated that units of osmolarity could also be used.

In some embodiments, the enclosed volume 106 can swell from a first diameter 110 to a second diameter 112. The closer the enclosed volume 106 approaches the size of the lymphatic vessel lumen 114, the more it occludes the flow of fluid through the renal lymphatic vessel 108. Complete or partial occlusion of the lymphatic vessel lumen 114 can result in modulating renal function so as to excrete more fluid, achieving a result similar to the administration of diuretic therapeutic agents.

Figure 2:
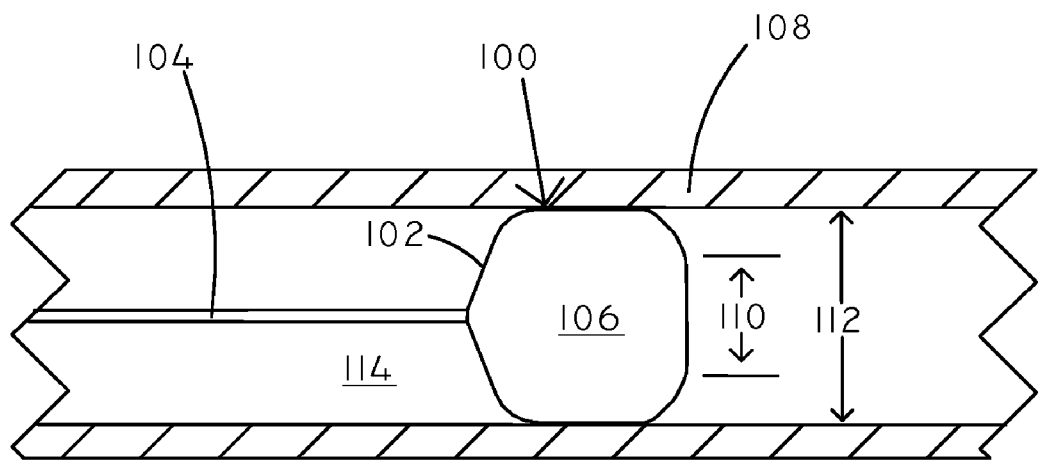
FIG. 2 is a schematic view of the occlusive device of FIG. 1 in an expanded configuration.

Referring now to FIG. 2, a schematic view of the occlusive device of FIG. 1 is shown in an expanded configuration. In this view, the enclosed volume 106 is expanded to a degree that the occlusive device 100 is now occluding substantially the entire lumen 114 of the renal lymphatic vessel 108. It will be appreciated that the device 100 can be configured so that maximal expansion of the enclosed volume 106 occludes a particular percentage of the lumen of the renal lymphatic vessel 108. For example, in some embodiments, the device can be configured so that it occludes a maximum of approximately 50% of the cross-sectional area of the lumen 114 of the renal lymphatic vessel when the enclosed volume 106 is fully expanded. In some embodiments, the device can be configured so that it occludes a maximum of approximately 70% of the cross-sectional area of the lumen 114 of the renal lymphatic vessel when the enclosed volume 106 is fully expanded. In some embodiments, the device can be configured so that it occludes a maximum of approximately 90% of the cross-sectional area of the lumen 114 of the renal lymphatic vessel when the enclosed volume 106 is fully expanded. In some embodiments, the device can be configured so that it occludes approximately 100% of the cross-sectional area of the lumen 114 of the renal lymphatic vessel when the enclosed volume 106 is fully expanded.

Figure 3:
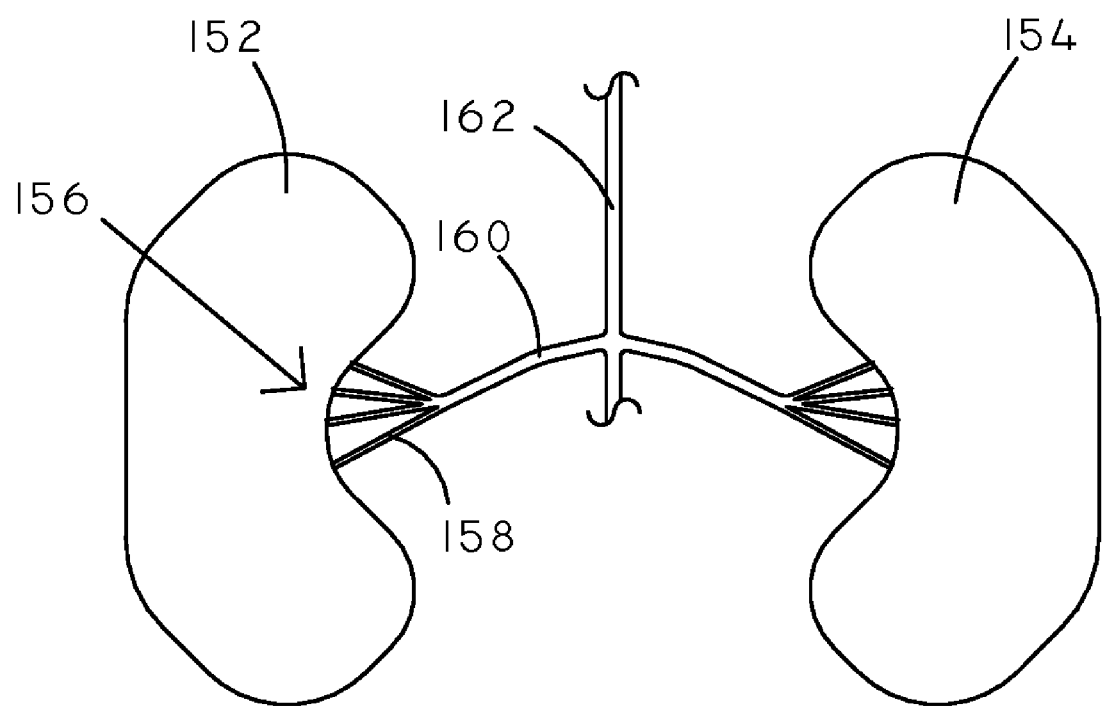
FIG. 3 is a schematic view of portions of the renal lymphatic system.

Occlusive devices in accordance with embodiments of the invention can be placed into various locations in the body in order to modulate renal function. Referring now to FIG. 3, a schematic view is shown of portions of the renal lymphatic system. FIG. 3 shows a right kidney 152 and a left kidney 154. Renal lymphatic vessels 158 can emerge from the kidney near the Hilar region 156 of the kidney. The renal lymphatic vessels 158 can serve to carry lymphatic fluid. The renal lymphatic vessels 158 can join together to form a renal lymphatic vessel trunk 160. The renal lymphatic vessel trunk 160 passes the lymphatic fluid on to the thoracic duct 162. One or more occlusive devices, as described herein, can be positioned appropriately to block or reduce the flow of lymphatic fluid through the renal vessels including individual vessels 158 and the vessel trunk 160 as well as the thoracic duct 162 itself. As used herein, the term "renal lymphatic vessel" shall include both the individual vessels and the vessel trunk. The occlusive devices can be placed inside of or adjacent to the individual vessels 158 or the trunk 160. In some embodiments, an occlusive device can be positioned on or within the thoracic duct 162.

Figure 4:
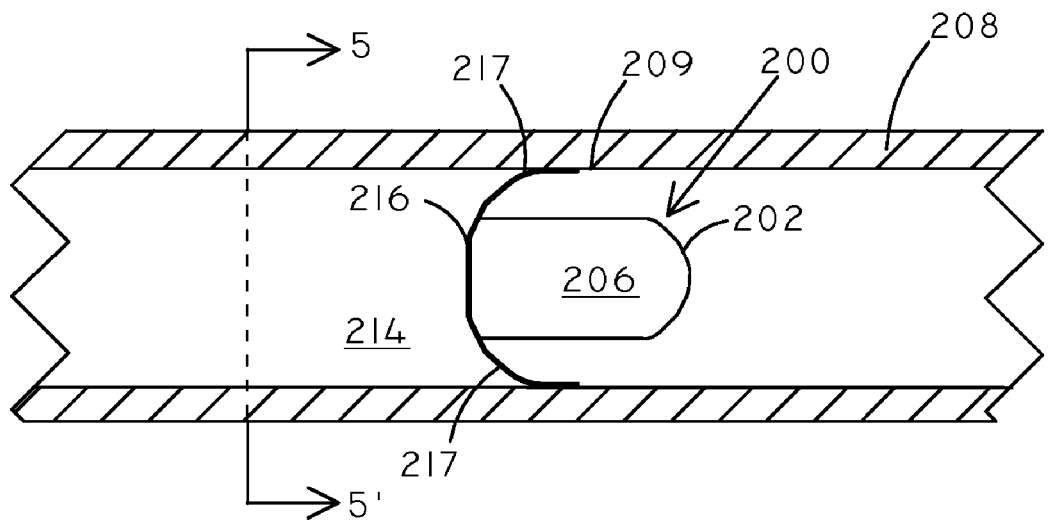
FIG. 4 is a schematic view of an untethered occlusive device in accordance with an embodiment of the invention.

In some embodiments, the occlusive device can be untethered. For example, the occlusive devices themselves can include a retention member to maintain their position within the lumen of a renal lymphatic vessel. Referring now to FIG. 4, an embodiment of an untethered occlusive device 200 is shown in accordance with an embodiment of the invention. The occlusive device 200 includes a wall member 202 that includes a semi-permeable membrane. The wall member 202 surrounds an enclosed volume 206, separating the enclosed volume 206 from the lumen 214 of the renal lymphatic vessel 208. A retention member 216 can be coupled to the wall member 202. The retention member 216 can be configured to engage the inside surfaces 209 of the renal lymphatic vessel 208. The retention member 216 can include one or more arms 217 or appendages.

Figure 5:
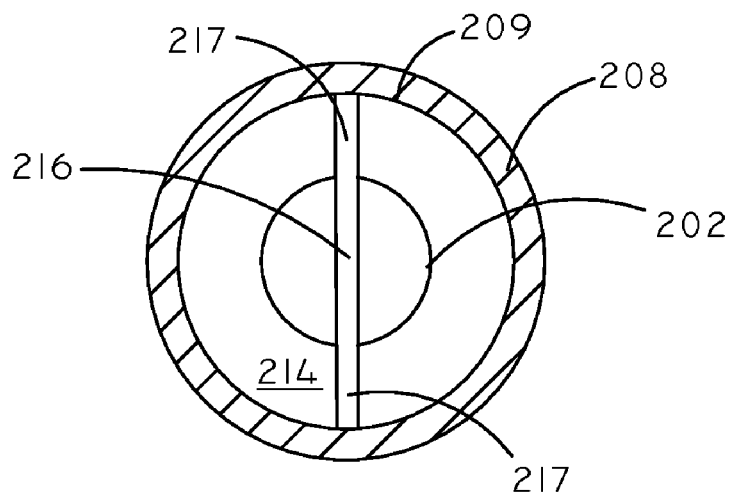
FIG. 5 is a cross-sectional schematic view as taken along line 5-5' of FIG. 4.

Referring now to FIG. 5, a cross-sectional schematic view of the renal lymphatic vessel is shown as taken along line 5-5' of FIG. 4. In this view, the retention member 216 can be seen engaging the inside surface 209 of the renal lymphatic vessel 208. In some embodiments, the retention member 216 can be configured so that it exerts a force against the inside surface 209 of the renal lymphatic vessel 208.

Figure 6:
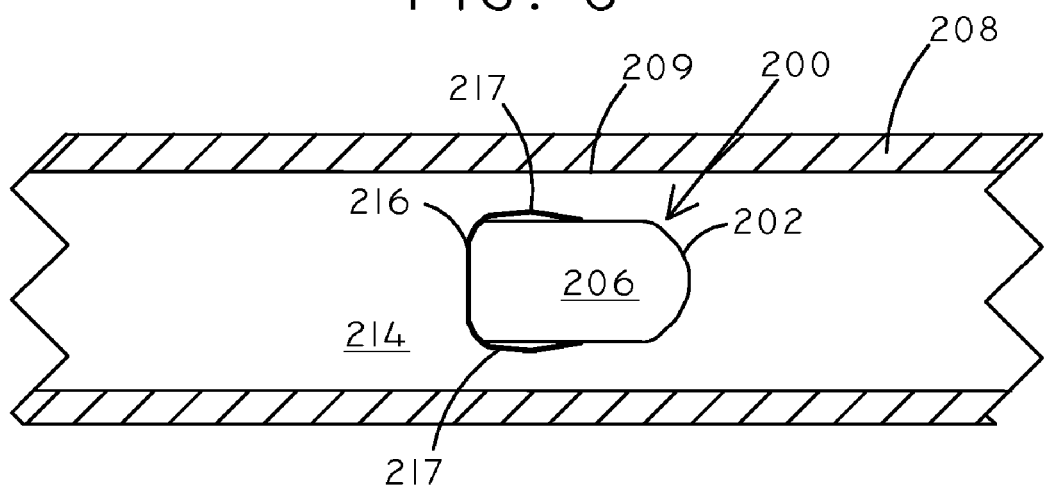
FIG. 6 is a schematic view of the device of FIG. 4 in a different configuration.

Referring now to FIG. 6, the retention member 216 can exhibit a degree of elasticity so that the arms 217 or appendages of the retention member 216 can be disposed against the wall member 202 to facilitate inserting the occlusive device 200 into a desired location within the renal lymphatic vessel system. For example, a sheath (not shown) can be disposed over the arms 217 when the occlusive device 200 is being inserted into the proper position. In this configuration, the effective diameter of the retention member is smaller than the diameter of the lumen 214. Then, after the occlusive device has been maneuvered into the desired position, the sheath can be removed allowing the arms 217 to flex outwardly and engage the inside surface 209 of the renal lymphatic vessel 208.

The retention member 216 can include many different materials. By way of example, the retention member 216 can include polymers, metals, metal alloys, ceramics, and the like. In some embodiments, the retention member 216 is a shape memory material, such as a shape memory metal. In an embodiment, the retention member 216 is the alloy nitinol. In the embodiment shown in FIGS. 4-6, the retention member 216 has two arms. However, it will be appreciated that in other embodiments the retention member can have a different number of arms. By way of example, the retention member can include three arms, four arms, or more than four arms. It will be appreciated that the retention member can also take on different shapes. By way of example, in some embodiments, the retention member can have a substantially annular shape. The retention member can also include a tubular mesh configuration similar to shape of vascular stents. The retention member can serve as an example of a positioning member since it can serve to maintain the position of the occlusive device relative to the lengthwise axis of the renal lymphatic vessel (axis of fluid flow) in which it can occlude fluid flow.

In some embodiments, the wall member of the occlusive device can include a non-permeable membrane (non-permeable to both solvents and solutes) in addition to the semi-permeable membrane. For example, the wall member can include a semi-permeable membrane in areas where it is desired to have fluids diffuse through and can include a non-permeable membrane in other areas. In some embodiments, a non-permeable portion of the wall member can be used to enhance the structural characteristics of the device. In addition, a non-permeable portion of the wall member can be used to control how the enclosed volume of the occlusive device expands, such as the direction in which it expands.

Figure 7:
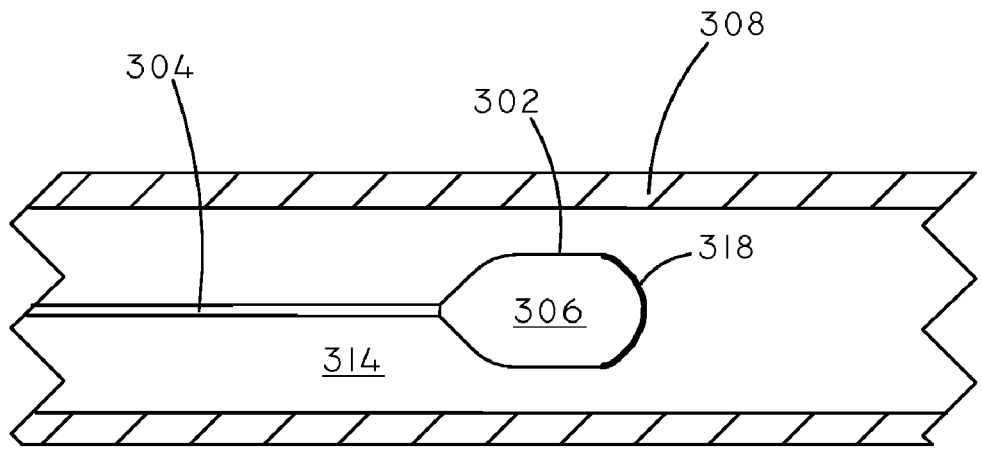
FIG. 7 is a schematic view of an occlusive device disposed within the lumen of a lymphatic vessel in accordance with another embodiment of the invention.

Referring now to FIG. 7, a schematic view is shown of an occlusive device disposed within the lumen 314 of a lymphatic vessel 308 in accordance with another embodiment of the invention. A wall member 302 including a semi-permeable membrane encloses an enclosed volume 306. The wall member 302 is attached to a lead member 304. The lead member can serve to maintain the position of the occlusive device. A solution including a solvent and a solute is disposed within the enclosed volume 306. The wall member 302 can include a non-permeable portion 318 or patch (impermeable to both the solvent and the solute). In some embodiments, the non-permeable portion 318 is joined at its perimeter to the semi-permeable membrane. In some embodiments, the non-permeable portion 318 is disposed on top of the semi-permeable membrane. In some embodiments, the non-permeable portion 318 is adhered to the semi-permeable membrane, such as with an adhesive. In some embodiments, the non-permeable portion 318 is welded to the semi-permeable membrane.

Figure 8:
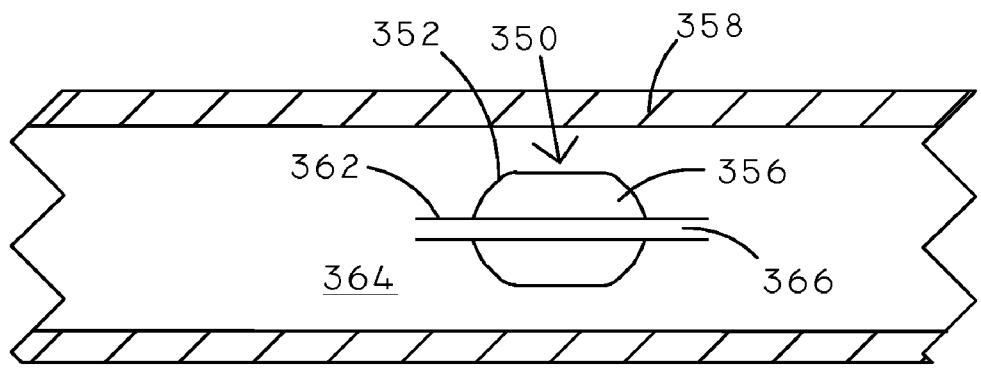
FIG. 8 is a schematic view of an occlusive device disposed within the lumen of a lymphatic vessel in accordance with another embodiment of the invention.

In some applications it may be desirable to ensure that some percentage of the lymphatic vessel remains open to the flow of lymphatic fluid. As such, in some embodiments, an occlusive device can include a central lumen or channel that provides a passageway for lymphatic fluid, regardless of the state of expansion of the occlusive device. Referring now to FIG. 8, an embodiment of an occlusive device 350 with a channel is shown disposed within the lumen 364 of a lymphatic vessel 358 in accordance with an embodiment of the invention. A wall member 352 including a semi-permeable membrane encloses an enclosed volume 356. A solution including a solvent and a solute is disposed within the enclosed volume 356.

Figure 9:
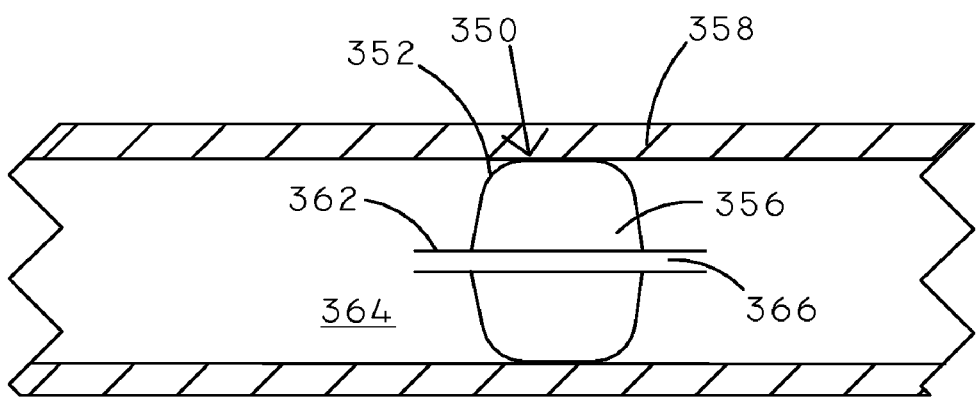
FIG. 9 is a schematic view of the occlusive device of FIG. 8 is a different configuration.

The wall member 352 is coupled to a channel member 362 defining a device lumen 366. The channel member 362 can include a cylindrical-type shape, resisting deformation when the enclosed volume 356 expands and contracts. For example, the channel member 362 can include a polymeric or metallic tube. The device lumen 366 can serve as a passageway for lymphatic fluid regardless of the degree of expansion of the enclosed volume 356. Referring now to FIG. 9, the occlusive device 350 of FIG. 8 is shown in an expanded configuration. In this view it can be seen that enclosed volume 356 has expanded to the bounds of the interior of the lymphatic vessel 358 and that the device lumen 366 still provides a passageway for lymphatic fluid. The device lumen 366 can have a cross-sectional area as large as is desired for the specific application. In some embodiments, the device lumen 366 includes a cross-sectional area equal to at least about 5% of the total cross-sectional area of the lumen 364 of the lymphatic vessel 358. In some embodiments, the device lumen 366 includes a cross-sectional area equal to at least about 10% of the total cross-sectional area of the lumen 364 of the lymphatic vessel 358.

Figure 10:
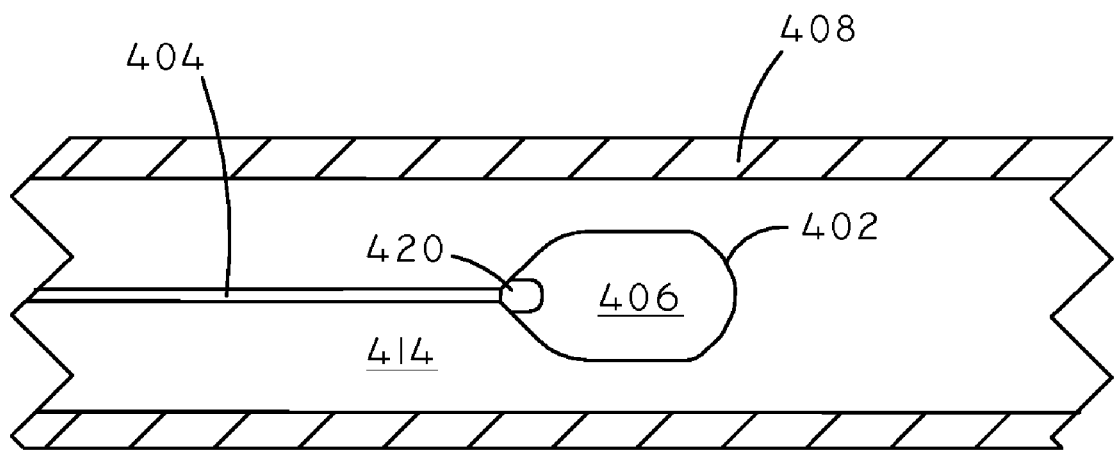
FIG. 10 is a schematic view of an occlusive device with a sensor disposed within the lumen of a lymphatic vessel in accordance with another embodiment of the invention.

In some circumstances, it can be desirable to monitor the status of the occlusive device in vivo. In some embodiments, the occlusive device includes a sensor so that the status and degree of expansion of the occlusive device can be monitored. Referring now to FIG. 10, an occlusive device with a sensor 420 is shown disposed within the lumen 414 of a lymphatic vessel 408 in accordance with another embodiment of the invention. A wall member 402 including a semi-permeable membrane encloses an enclosed volume 406. A solution including a solvent and a solute is disposed within the enclosed volume 406. A sensor 420 can be in communication with the enclosed volume 406. The wall member 402 is coupled to a lead member 404. The lead member 404 can serve to maintain the position of the occlusive device. The lead member 404 can also include an electrical or an optical conductor in order to convey signals to or from the sensor 420.

The sensor 420 can be configured to sense various properties that are indicative of the status and performance of the occlusive device. In some embodiments, the sensor 420 can be configured to sense pressure within the enclosed volume 406 of the occlusive device. The sensor 420 can include any type of pressure sensor, for example an electrical, mechanical, or optical pressure sensor, that generates a signal in response to pressure. By way of example, exemplary pressure sensors are described in U.S. Pat. No. 6,237,398, the content of which is herein incorporated by reference.

In some embodiments, the sensor 420 can be configured to sense the osmolality within the enclosed volume 406. Generally, it is expected that the osmolality within the enclosed volume 406 will reflect the osmolality of the bodily fluid surrounding the occlusive device since fluid can diffuse through the semi-permeable membrane in order to equalize osmolalities. However, sudden large changes in osmolality can be indicative of dysfunction of the patient or of the device itself. As such, in some embodiments, signals from the sensor 420 can pass through the lead member 404 to a monitoring device which can be configured to monitor for changes in sensed osmolality. Many different types of osmolality sensors can be used. One example of an osmolality sensor is described in U.S. Pat. No. 5,388,449, the contents of which is herein incorporated by reference.

In some embodiments, the sensor 420 can be configured to sense the physical dimensions of enclosed volume 406. For example, the sensor 420 can be configured to sense the diameter of the enclosed volume 406 and/or the length of the enclosed volume 406. Specifically, the sensor 420 can include photosensor with a light source, such as a light emitting diode (LED), and a light receiver, such as a charge-coupled device (CCD), photodiode, a junction field effect transistor (JFET) type optical sensor, or a complementary metal-oxide semiconductor (CMOS) type optical sensor. The light source can generate an emission of light within the enclosed volume 406 that reflects off an opposing part of the wall member before being received by the light receiver. The larger the size of the enclosed volume 406, the farther the light must travel and the greater the loss of light intensity due to diffusion. Therefore, the intensity of light received by the light receiver can be correlated to the size of the enclosed volume. It will be appreciated that this is merely one example of a sensor for detecting the physical dimensions of the enclosed volume and that there are also many other types of sensors that can also be used to sense the size of the enclosed volume.

Figure 11:
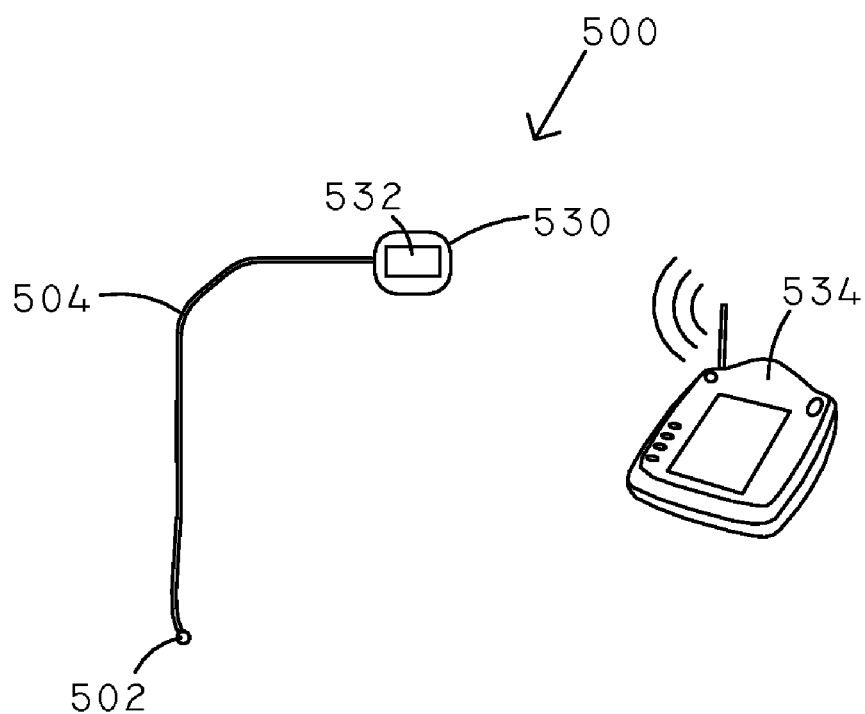
FIG. 11 is a schematic view of a monitoring device in conjunction with an occlusive device in accordance with an embodiment of the invention.

In some embodiments, signals from the sensor can pass through the lead member to a monitoring device. Referring now to FIG. 11 a schematic view of a system 500 including a monitoring device 530 in conjunction with an occlusive device 502 is shown in accordance with an embodiment of the invention. The monitoring device 530 can include a controller module 532. The monitoring device 530 can be coupled to a lead 504 which is in turn coupled to an occlusive device 502 that includes a sensor. However, it will be appreciated that in some embodiments, the monitoring device 530 and the occlusive device 502 can be in wireless communication.

A remote monitoring device 534 can also be included and can be in wireless communication with the monitoring device 530. For example, data regarding the occlusive device 502, as stored by the controller 532, can be wirelessly transmitted to the remote monitoring device 534. The remote monitoring device 534 can be a patient management system. An exemplary patient management system includes the LATITUDE® patient management system, commercially available from Boston Scientific Corporation, Natick, Mass. Aspects of an exemplary patient management system are described in U.S. Pat. No. 6,978,182, the contents of which are herein incorporated by reference.

Figure 12:
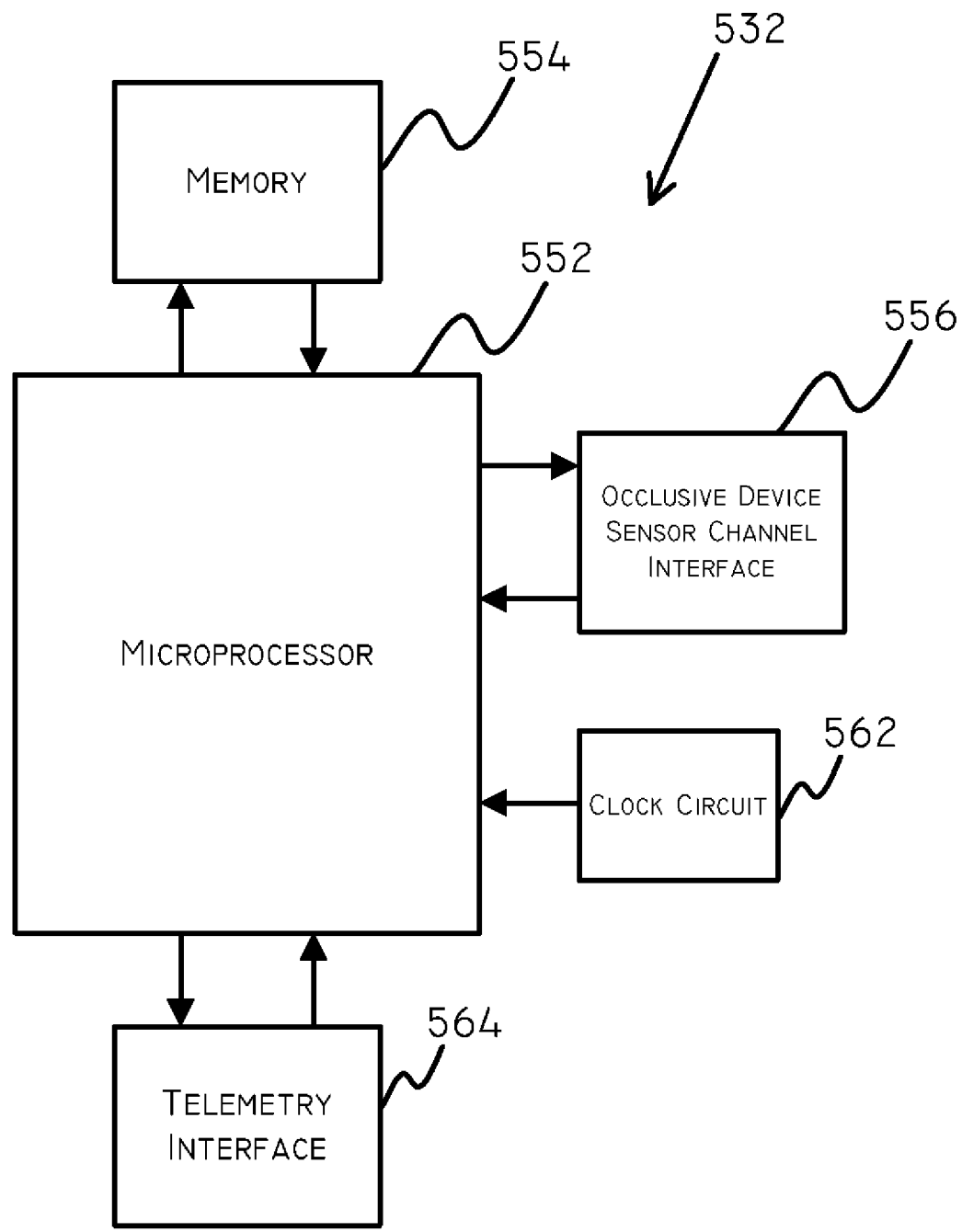
FIG. 12 is a schematic view of some aspects of a controller in accordance with an embodiment of the invention.

The controller 532 can include various electronic components and can be configured to process signals from a sensor within an occlusive device, including analyzing the signals and storing data regarding the signals. Referring now to FIG. 12, some aspects of a controller 532 are schematically illustrated. In this embodiment, the controller 532 includes a microprocessor 552 that communicates with memory 554 via a bidirectional data bus. The memory 554 typically comprises ROM or RAM for program storage and a RAM for data storage. The controller 532 can include a bidirectional occlusive device sensor channel interface 556. In addition, the controller 532 can include a clock circuit 562. The controller 532 can also include a telemetry interface module 564 for wireless communication of data into and out of the controller 532.

Figure 13:
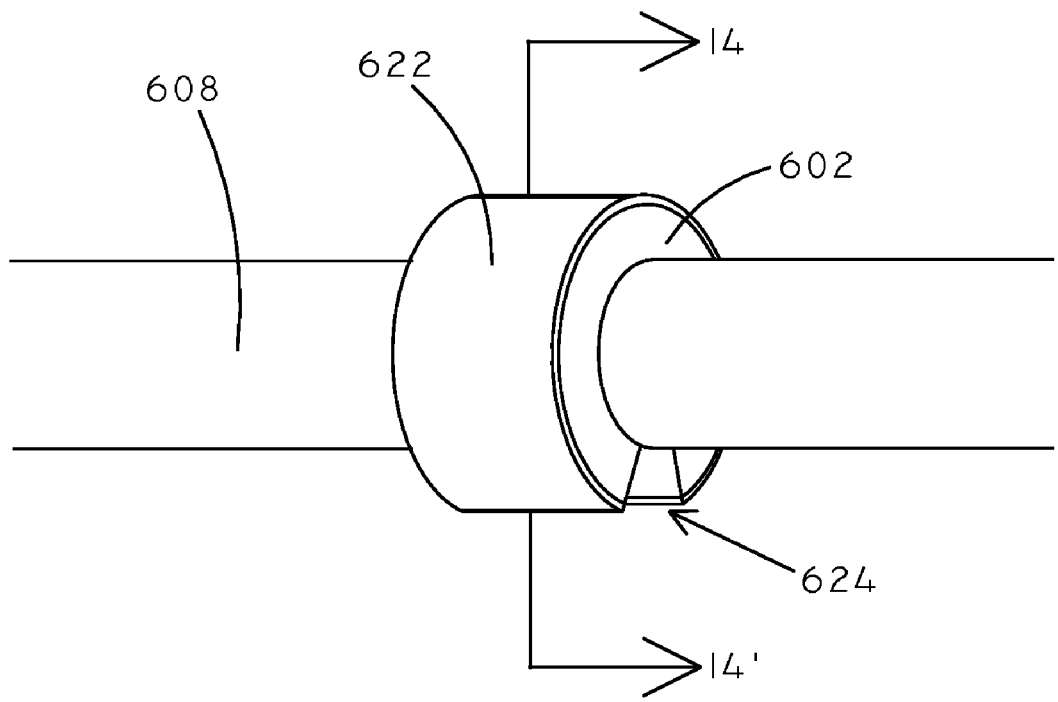
FIG. 13 is a schematic view of an occlusive device in accordance with another embodiment of the invention.

In some embodiments, the invention can include occlusive devices configured to be disposed on the outside of renal lymphatic vessels. Referring now to FIG. 13, an embodiment of an occlusive device is shown in accordance with another embodiment of the invention. The occlusive device can include a wall member 602 defining an enclosed volume 606 (shown in FIG. 14). The wall member 602 can include a semi-permeable membrane, examples of which are described in greater detail below. A semi-rigid support member 622 can be disposed around the outer perimeter of the wall member 602. The semi-rigid support member 622 can serve to maintain the occlusive device in position around the renal lymphatic vessel 608. The semi-rigid support member 622 can also serve as an example of a positioning member since it can serve to maintain the position of the occlusive device relative to the lengthwise axis of the renal lymphatic vessel 608 (axis of fluid flow) in which it can occlude fluid flow.

In some embodiments, the wall member 602 and the semi-rigid support member 622 can both have a shape similar to a ring with a gap 624 in the perimeter of the ring. This shape can also be referred to as a discontinuous annular shape. The occlusive device can be wrapped around a renal lymphatic vessel 608. The gap 624 in the wall member 602 and the semi-rigid support member 622 can allow the ring-shaped device to be opened so that it can be positioned around the renal lymphatic vessel 608.

Figure 14:
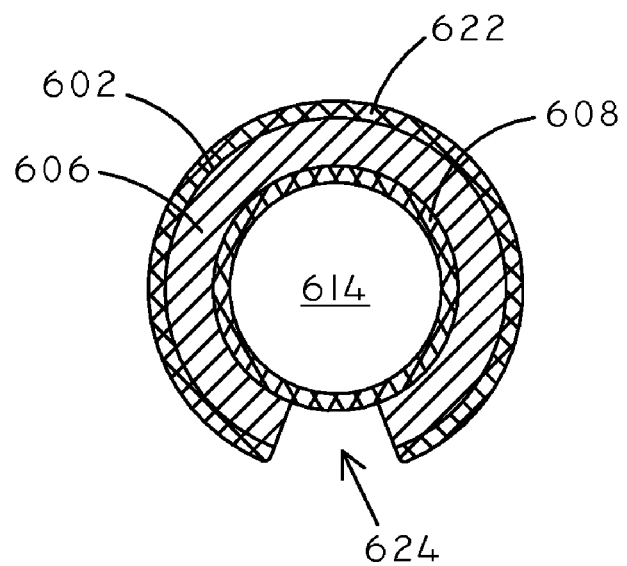
FIG. 14 is a cross-sectional view of the occlusive device of FIG. 13 as taken along line 14-14' of FIG. 13.

Referring now to FIG. 14, a cross-sectional view of the occlusive device of FIG. 13 is shown as taken along line 14-14' of FIG. 13. As the support member 622 is semi-rigid, it serves to direct expansion of the enclosed volume 606 inward toward the lumen 614 of the renal lymphatic vessel 608. In some embodiments, the support member can be made of a polymer or a metal.

Figure 15:
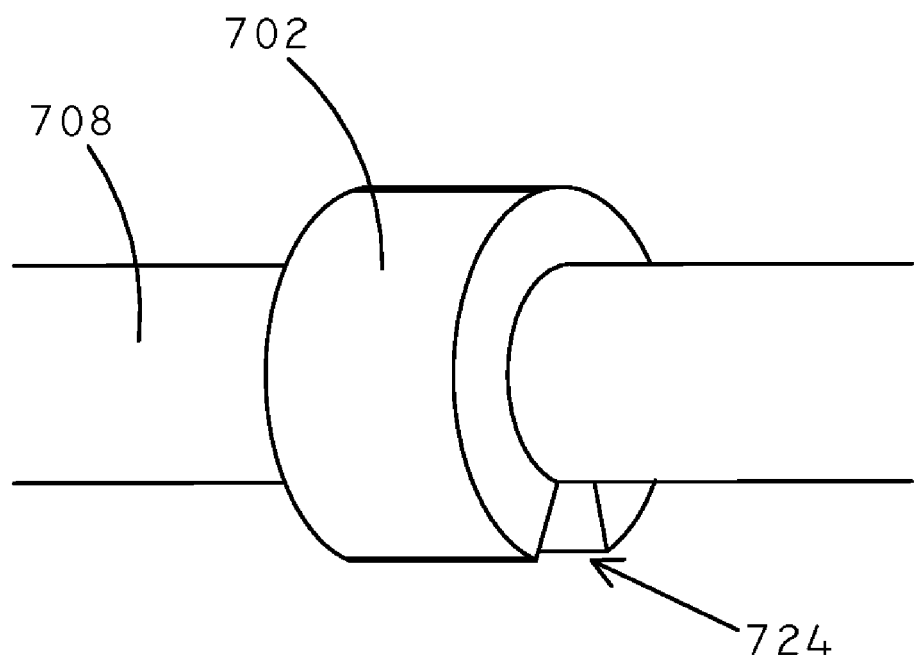
FIG. 15 is a schematic view of an occlusive device in accordance with another embodiment of the invention.

However, some embodiments of occlusive devices configured to be disposed outside of renal lymphatic vessels can lack support members. For example, referring now to FIG. 15, an embodiment of an occlusive device is shown lacking a support member. The occlusive device can include a wall member 702 defining an enclosed volume. The wall member 702 can include a semi-permeable membrane, examples of which are described in greater detail below. The occlusive device can be wrapped around a renal lymphatic vessel 708. A gap 724 in the wall member 706 can allow the device to be opened so that it can be wrapped around the renal lymphatic vessel 708.

In some embodiments, the enclosed volume of the occlusive device can be filled with a solution including a solvent and a solute when the device is first manufactured. For example, in some embodiments, a solution with an osmolality of between about 280 and about 303 mOsm/kg is disposed within the enclosed volume when the device is initially manufactured. However, in other embodiments, the device can be configured so that it can be filled up with a solution having a desired solute concentration just before insertion into the patient. For example, in general, the use of solutions with higher concentrations of solute will result in greater initial swelling or enlargement of the enclosed volume of the device after it is positioned within the patient. As such, in some embodiments, the solute concentration of the solution can be manipulated by the clinician before implantation. For example, if the device is to be disposed within or around a particularly large renal lymphatic vessel, the starting osmolality of the solution within the enclosed volume can be increased so that there will be greater initial swelling or enlargement of the occlusive device. However, in other circumstances, where a smaller size is desired, a solution with a lesser concentration of solute can be inserted into the device before implantation into a patient. In some embodiments, a kit is provided including an occlusive device as described herein and a set of solutions with different solute concentrations, from which a health professional can select for use.

Figure 16:
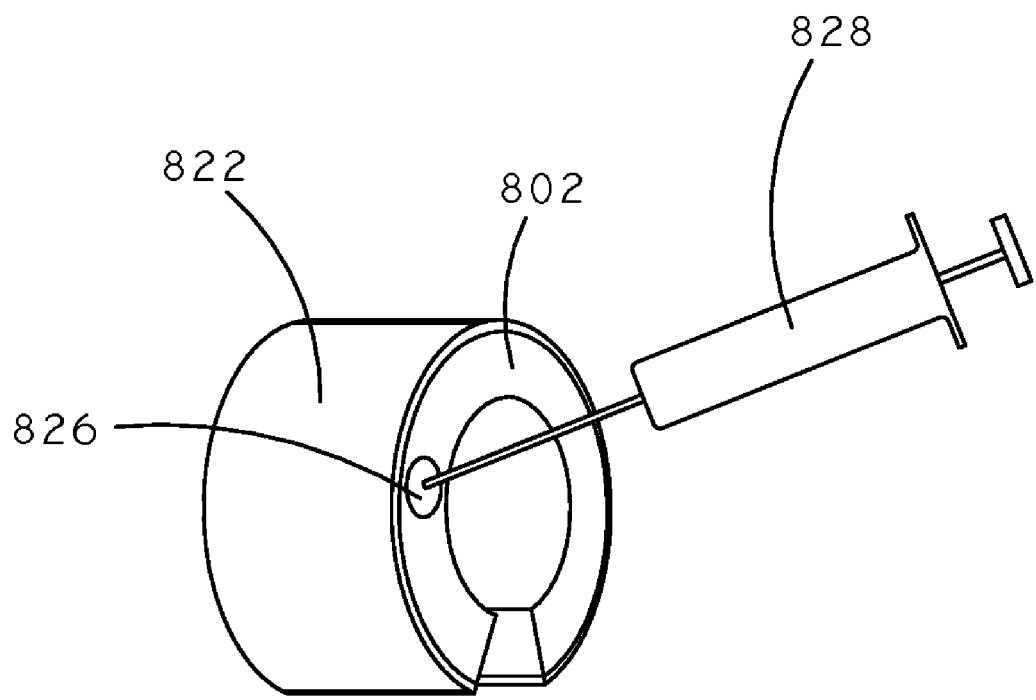
FIG. 16 is a schematic view of an occlusive device in accordance with another embodiment of the invention.

Referring now to FIG. 16, an embodiment of an occlusive device with an injection port is shown. The occlusive device can include a wall member 802 defining an enclosed volume. The wall member 802 can include a semi-permeable membrane, examples of which are described in greater detail below. A semi-rigid support member 822 can be disposed around the outer perimeter of the wall member 802. An injection port 826 can be disposed on the wall member 802. The injection port 826 can allow a syringe 828 to be inserted into the device to deliver a solution into the enclosed volume of the device. The injection port 826 can include a plug of material that self-seals to prevent leakage once the needle of the syringe 828 is withdrawn. For example, in an embodiment the injection port 826 can include a polymer with elastomeric properties. In an embodiment, the injection port 826 can include a polysiloxane polymer.

Figure 17:
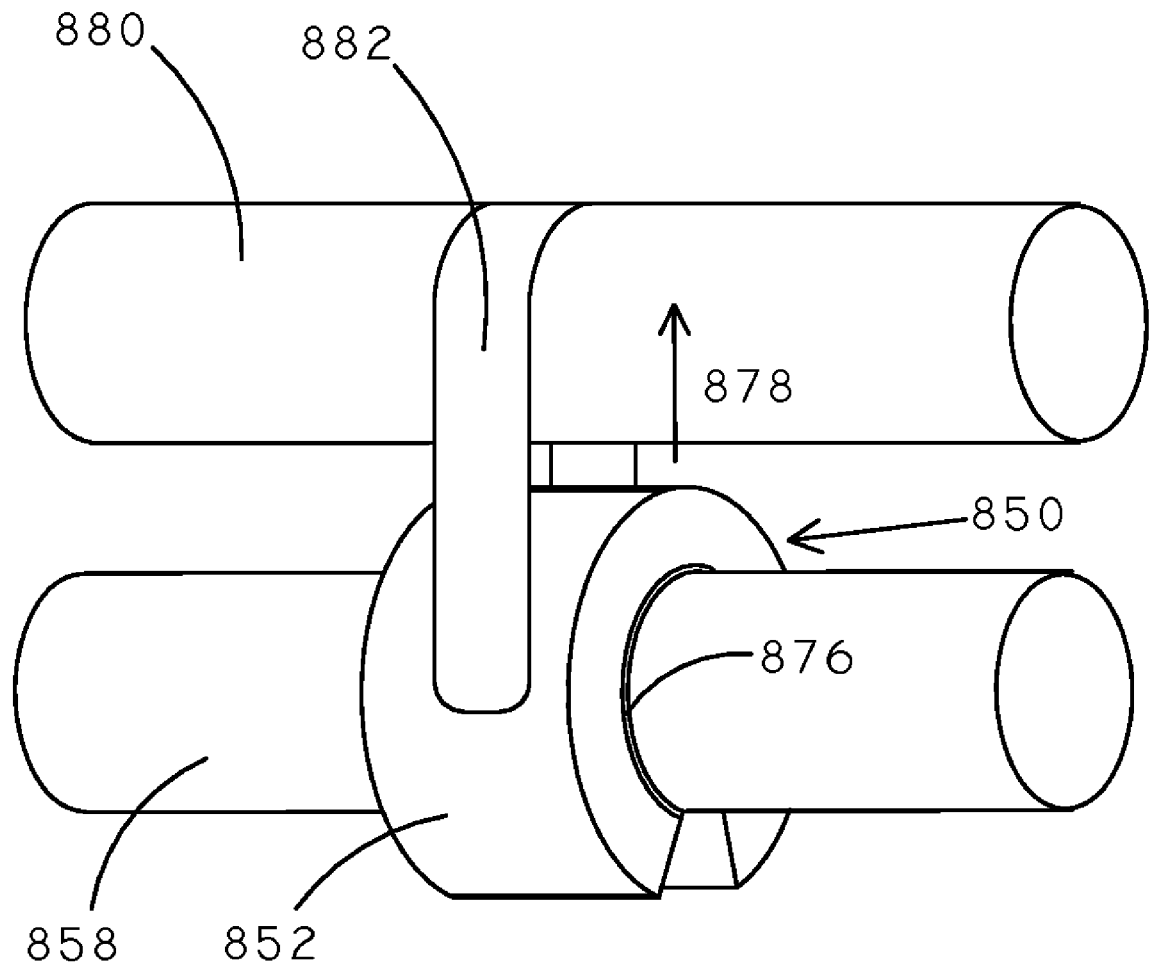
FIG. 17 is a schematic view of an occlusive device in accordance with another embodiment of the invention.

In some embodiments, an occlusive device can be disposed adjacent to a renal lymphatic vessel and can be configured to expand in a direction that results in occlusion of the renal lymphatic vessel. Referring now to FIG. 17, an occlusive device 850 is shown in accordance with another embodiment of the invention. The occlusive device 850 can include a wall member 852 defining an enclosed volume. The wall member 852 can include a semi-permeable membrane, examples of which are described in greater detail below. A semi-rigid support member 876 can be disposed around the inner perimeter of the wall member 852. In some embodiments, the semi-rigid support member 876 can include a semi-permeable membrane. The occlusive device 850 can be wrapped around a first vessel 858, which could be any type of vessel-like structure such as an artery or a vein. The enclosed volume can expand in the direction of arrow 878 as a result of changes in osmolality in the bodily fluid surrounding the device 850. Expansion can occur to an extent that the device 850 exerts a force on an adjacent renal lymphatic vessel 880 and occludes the same. The semi-rigid support member 876 can prevent expansion of the enclosed volume from occluding the first vessel 858 and focus expansion in an outward direction. A harness 882 or strap can be included so as to prevent the adjacent renal lymphatic vessel 880 from simply moving away when the device 850 expands. The harness 882 can include a loop of material wrapped around the adjacent renal lymphatic vessel 880. The harness 882 can also serve as an example of a positioning member since it can serve to maintain the position of the occlusive device relative to the lengthwise axis of the lymphatic vessel (axis of fluid flow) in which it can occlude fluid flow.

In some cases, it may be desirable to configure the device to be more directly responsive to changes in osmolality within arteries and/or veins. In some embodiments, the occlusive device can include a finger like projection or protruding member that passes from a wall member, through an aperture in the wall of an artery or vein, and into the interior lumen of the artery or vein. The projection can include a semi-permeable membrane and can be in fluid communication with an enclosed volume of the occlusive device. In some embodiments, other portions of the occlusive device are impermeable. As such, expansion and contraction of the occlusive device can be made to be particularly sensitive to changes in osmolality in plasma within the lumen of an artery or vein.

Figure 18:
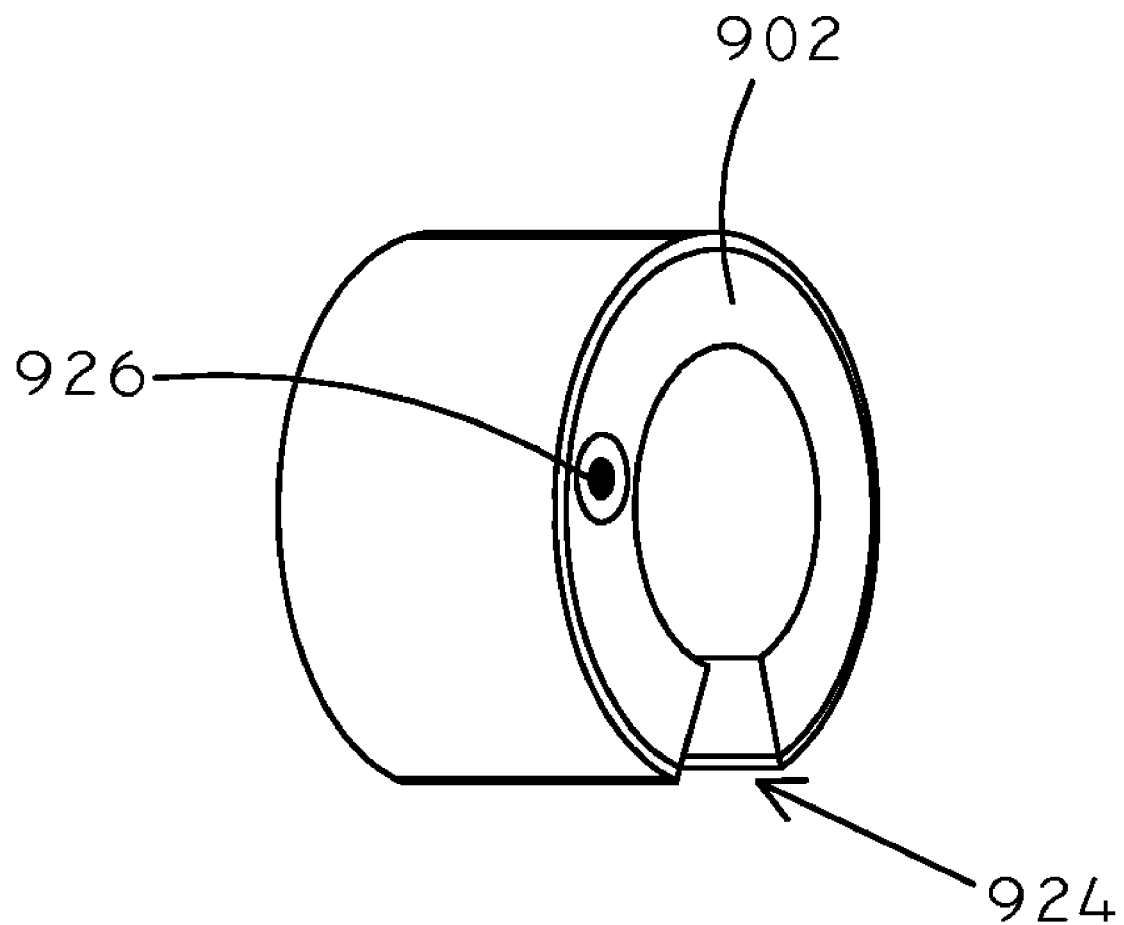
FIG. 18 is a schematic view of an occlusive device in accordance with another embodiment of the invention.

In some embodiments, over-expansion of the device can be controlled for purposes of safety. Various techniques and structures can be used to prevent over-expansion. For example, in an embodiment, an inflexible band can be disposed over the device, the inflexible band having a circumference corresponding to the maximum allowable size of the occlusive device. In another embodiment, the device can include a pressure release valve, the valve configured to open when a certain threshold pressure is reached inside of the occlusive device. Referring now to FIG. 18, an embodiment of an occlusive device with a pressure release valve is shown. The occlusive device can include a wall member 902 defining an enclosed volume. The wall member 902 can include a semi-permeable membrane, examples of which are described in greater detail below. A pressure release valve 926 can be disposed on the wall member 902. The pressure release valve 926 can be configured to open when the pressure in the area enclosed by the wall member 902 exceeds a threshold amount. As such, the pressure inside of the enclosed volume is prevented from becoming so high that the wall member 902 could rupture or that the area enclosed by the wall member 902 becomes undesirably large. Many different types of pressure release valves 926 are known to those of skill in the art and can be used.

Semi-Permeable Membranes

Embodiments of the invention can include a semi-permeable membrane. The term "semi-permeable membrane" as used herein shall refer to a membrane that is permeable to a solvent but impermeable to one or more solutes, such that the semi-permeable membrane can be used in the process of osmosis. Exemplary solutes can include chemical compounds found within bodily fluids such as salts and their ions including calcium ions, sodium ions, potassium ions, chlorine ions, glucose and other carbohydrates, proteins (such as albumin), glycosaminoglycans, and the like. The term "impermeable" as applied to an article, such as a membrane, shall refer to one that substantially blocks the passage of one or more compounds through its substance.

It will be appreciated that semi-permeable membranes can be constructed of many different types of materials. For example, semi-permeable membranes can include polymers such as cellulose, cellulose derivatives, polyacrylonitrile, polysulfone, polycarbonates, polyamides, polymethyl-methacrylate (PMMA), polyethylenes, polytetrafluoroethylene (PTFE), and polysiloxanes. In some embodiments, the semi-permeable membrane can include a hydrogel. The specific choice of material can depend on factors such as desired tear strength, desired flexibility, and the like. In an embodiment, the semi-permeable membrane includes a biocompatible material.

In some embodiments, the semi-permeable membrane can be porous. The pores can have a diameter large enough to allow for the passage of water molecules but small enough to prevent the passage of various solutes found in bodily fluids.

Figure 19:
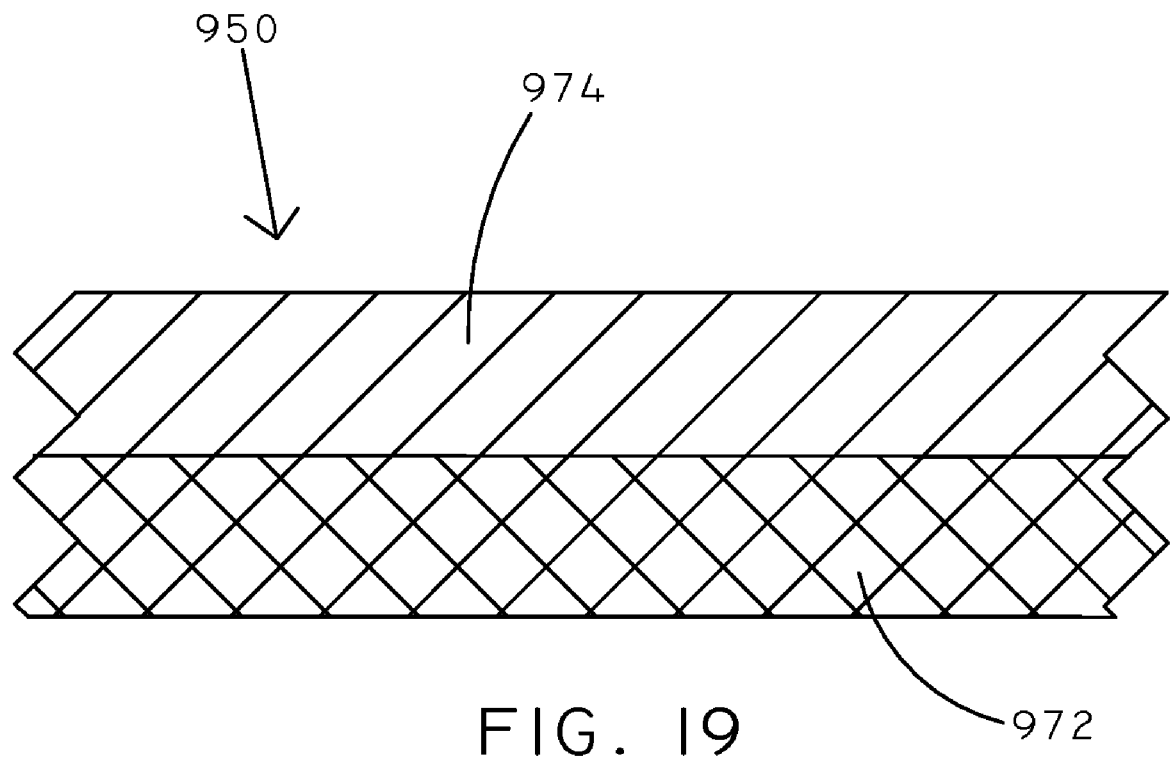
FIG. 19 is a schematic view of a multi-layer membrane structure in accordance with an embodiment of the invention.

The semi-permeable membrane can have a thickness that is sufficient to provide strength to prevent tearing under the conditions of use. However, the semi-permeable membrane can be thin enough to maintain flexibility. In some embodiments, the semi-permeable membrane is between about 1 nanometer and about 2 millimeters in thickness. In some embodiments, a semi-permeable membrane can include multiple layers of material. For example, referring to FIG. 19, an embodiment of a multi-layer semi-permeable membrane 950 structure is shown. A first layer 972 is disposed beneath a second layer 974. The first layer 972 and second layer 974 can include the same materials or different materials. In some embodiments, the first layer 972 is fastened to the second layer 974. For example, an adhesive can be disposed between the first layer 972 and the second layer 974. In some embodiments, the first layer 972 and the second layer 974 are thermally welded together, such as through ultrasonic welding or a similar technique.

In some embodiments, the semi-permeable membrane can have an irregularly shaped surface or various types of surface features such as dimples in order to increase its effective surface area.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. An implantable occlusive device comprising:
   a wall member defining an enclosed volume, the wall member comprising a semi-permeable membrane;
   a solution comprising a solvent and a solute, the solution disposed within the enclosed volume; and
   a positioning member, the positioning member configured to maintain the position of the implantable occlusive device relative to a lengthwise axis of a lymphatic vessel;
   the semi-permeable membrane permeable to the solvent and impermeable to the solute;
   the enclosed volume configured to expand in response to decreases in osmolality of a bodily fluid and contract in response to increases in osmolality of a bodily fluid;
   wherein the wall member and enclosed volume are configured to be fully implanted within a patient.

2. The implantable occlusive device of claim 1, the semi-permeable membrane comprising a biocompatible material.

3. The implantable occlusive device of claim 1, the solute comprising at least one of sodium chloride and potassium chloride.

4. The implantable occlusive device of claim 1, the semi-permeable membrane comprising a polymer.

5. The implantable occlusive device of claim 4, the semi-permeable membrane comprising polytetrafluoroethylene.

6. The implantable occlusive device of claim 1, the wall member further comprising a membrane impermeable to both the solvent and the solute.

7. The implantable occlusive device of claim 6, the impermeable membrane configured to control how the enclosed volume expands.

8. The implantable occlusive device of claim 6, the impermeable membrane joined at its perimeter to the semi-permeable membrane.

9. The implantable occlusive device of claim 6, the impermeable membrane disposed on top of the semi-permeable membrane.

10. The implantable occlusive device of claim 1, the positioning member comprising a rigid support member disposed around an outer perimeter of the enclosed volume.

11. The implantable occlusive device of claim 10, the rigid support member comprising an annular shape.

12. The implantable occlusive device of claim 1, further comprising an osmolality sensor configured to sense the osmolality of the solution within the enclosed volume.

13. The implantable occlusive device of claim 1, further comprising a pressure sensor configured to sense the pressure within the enclosed volume.

14. The implantable occlusive device of claim 1, the positioning member comprising a lead body coupled to the wall member.

15. The implantable occlusive device of claim 8, further comprising a conductor disposed within the lead body.

16. The implantable occlusive device of claim 1, the positioning member comprising one or more appendages configured to engage an inside surface of a renal lymphatic vessel.

* * * * *